(12) United States Patent
Hong et al.

(10) Patent No.: US 11,596,369 B2
(45) Date of Patent: Mar. 7, 2023

(54) NAVIGATION SYSTEM FOR VASCULAR INTERVENTION AND METHOD FOR GENERATING VIRTUAL X-RAY IMAGE

(71) Applicant: Daegu Gyeongbuk Institute of Science and Technology, Daegu (KR)

(72) Inventors: Jae-Sung Hong, Daegu (KR); Sang-Seo Jeon, Wonju-si (KR); Seong-Pung Lee, Daegu (KR)

(73) Assignee: DAEGU GYEONGBUK INSTITUTE OF SCIENCE AND TECHNOLOGY, Daegu (KR)

( * ) Notice: Subject to any disclaimer, the term of this patent is extended or adjusted under 35 U.S.C. 154(b) by 457 days.

(21) Appl. No.: 15/499,116

(22) Filed: Apr. 27, 2017

(65) Prior Publication Data

US 2017/0319156 A1 Nov. 9, 2017

(30) Foreign Application Priority Data

May 3, 2016 (KR) .................. 10-2016-0054755
Apr. 12, 2017 (KR) .................. 10-2017-0047421

(51) Int. Cl.
*A61B 6/12* (2006.01)
*A61B 6/00* (2006.01)
(Continued)

(52) U.S. Cl.
CPC .............. *A61B 6/12* (2013.01); *A61B 6/466* (2013.01); *A61B 6/5205* (2013.01); *A61B 34/20* (2016.02);
(Continued)

(58) Field of Classification Search
CPC ......... A61B 6/12; A61B 90/36; A61B 6/5205; A61B 6/466; A61B 34/20; A61B 2017/00725; A61B 2034/2051; A61B 2090/364; A61B 2090/3966; A61B 2090/376; A61B 2034/2068; A61B 2034/2065; A61B 2090/3983; A61B 2090/367; A61B 5/06; A61B 90/37; A61B 90/90; A61B 2090/365; A61B 6/5235; A61B 6/5247; A61B 2090/374; A61B 2090/3764; A61B 6/02; A61B 6/03; A61B 2090/3762; A61B 2090/397; A61B 2562/0228; A61B 2562/143; A61B 90/39; A61B 34/10; A61B 2090/3937; A61B 5/066; A61B 2019/5466; A61M 25/0108; G06F 19/34; G06F 3/0665; G05B 2219/40288; G05B 2219/40126; G05B 2219/37569; G01M 17/028;
(Continued)

(56) References Cited

U.S. PATENT DOCUMENTS

10,478,149 B2 * 11/2019 Tamersoy ............ A61B 6/4458
10,956,635 B1 * 3/2021 Douglas ................ G06F 17/18
(Continued)

*Primary Examiner* — Luther Behringer
*Assistant Examiner* — Amy Shafqat
(74) *Attorney, Agent, or Firm* — Lex IP Meister, PLLC (57) ABSTRACT

Provided is a method of generating a virtual x-ray image, the method including: obtaining a 3-dimensional (3D) image of a patient; determining a projection direction of the 3D image in consideration of a position relationship between an x-ray source of an x-ray device and the patient; and generating a virtual x-ray image by projecting the 3D image on a 2D plane in the determined projection direction.

11 Claims, 10 Drawing Sheets

(51) Int. Cl.
*A61B 34/20* (2016.01)
*A61B 90/00* (2016.01)

(52) U.S. Cl.
CPC ...... *A61B 90/36* (2016.02); *A61B 2034/2051* (2016.02); *A61B 2034/2065* (2016.02); *A61B 2034/2068* (2016.02); *A61B 2090/364* (2016.02); *A61B 2090/367* (2016.02); *A61B 2090/376* (2016.02); *A61B 2090/3966* (2016.02); *A61B 2090/3983* (2016.02)

(58) Field of Classification Search
CPC ...... G01N 23/20075; G01N 2223/1016; G03F 1/148; G03G 13/054; G03G 15/054; G06T 2207/10116; G06T 2207/10081; G06T 11/008; H03M 1/204; H01J 31/50; A61N 2005/1062; G03B 42/02
See application file for complete search history.

(56) References Cited

U.S. PATENT DOCUMENTS

| | | | |
|---|---|---|---|
| 11,206,998 B2* | 12/2021 | Lee | G01B 11/002 |
| 11,337,763 B2* | 5/2022 | Choi | A61B 6/5223 |
| 2002/0044631 A1* | 4/2002 | Graumann | A61B 6/547 |
| | | | 378/205 |
| 2002/0075994 A1* | 6/2002 | Shahidi | A61B 34/20 |
| | | | 378/62 |
| 2002/0085668 A1* | 7/2002 | Blumhofer | A61B 6/547 |
| | | | 378/68 |
| 2003/0179856 A1* | 9/2003 | Mitschke | A61B 90/36 |
| | | | 378/205 |
| 2005/0163279 A1* | 7/2005 | Mitschke | A61B 6/02 |
| | | | 378/62 |
| 2005/0281385 A1* | 12/2005 | Johnson | A61B 6/12 |
| | | | 378/163 |
| 2008/0317317 A1* | 12/2008 | Shekhar | G06T 3/0081 |
| | | | 382/131 |
| 2009/0003523 A1* | 1/2009 | Raanes | A61N 5/1049 |
| | | | 378/65 |
| 2010/0046718 A1* | 2/2010 | Weiser | A61B 6/583 |
| | | | 378/163 |
| 2010/0296623 A1* | 11/2010 | Mielekamp | A61B 6/032 |
| | | | 378/4 |
| 2011/0182492 A1* | 7/2011 | Grass | A61B 6/4441 |
| | | | 382/131 |
| 2013/0034203 A1* | 2/2013 | Wang | A61B 6/03 |
| | | | 378/41 |
| 2013/0094742 A1* | 4/2013 | Feilkas | A61B 6/584 |
| | | | 382/131 |
| 2015/0085979 A1* | 3/2015 | Zheng | A61B 6/584 |
| | | | 378/62 |
| 2017/0281111 A1* | 10/2017 | Van Geloof | G06T 19/00 |

* cited by examiner

NAVIGATION SYSTEM FOR VASCULAR INTERVENTION AND METHOD FOR GENERATING VIRTUAL X-RAY IMAGE

RELATED APPLICATION

This application claims the benefits of Korean Patent Applications No. 10-2016-0054755, filed on May 3, 2016 and No. 10-2017-0047421, filed on Apr. 12, 2017, in the Korean Intellectual Property Office, the disclosure of which is incorporated herein in its entirety by reference.

BACKGROUND OF THE INVENTION

1. Field of the Invention

The present disclosure relates to image processing fields, and more particularly, to a field of generating a virtual x-ray image from a 3-dimensional (3D) image or matching a local model of a 3D image to a virtual or actual x-ray image.

2. Description of the Related Art

Generally, vascular intervention is a surgical treatment for performing drug treatment and also stent insertion by percutaneously inserting a needle or a catheter into a vascular lesion based on a 3-dimensional (3D) image obtained by using an X-ray imaging apparatus without having to separately perform a surgical incision. In addition, since the x-ray imaging apparatus is able to easily determine an internal structure of a target object, the x-ray imaging apparatus is used to detect a disorder, such as a lesion, inside a human body in medical fields, or to determine an internal structure of an object or a component.

During general vascular intervention, a patient and a medical team may all be exposed to an excessive amount of radiation because x-ray imaging is frequently performed during a surgery in order to determine a position of a surgical instrument inserted in the body and a blood vessel state in real-time.

Moreover, since only a 2D x-ray image lacking depth information is referred to during the surgery, it is not easy to determine a 3D vascular structure and the position of the surgical instrument, and thus, for example, vascular perforation may occur if a catheter moves in a wrong path. Also, it is very difficult to determine a proceeding direction of the catheter in a region where the catheter is not visualized on an x-ray image because a contrast medium could not reach the region due to occlusion, and accordingly, accuracy and stability of the surgery tend to largely depend upon experience or skill of an operator.

Accordingly, a navigation system for vascular intervention, which has a new structure that increases accuracy and stability of the vascular intervention, needs to be developed.

SUMMARY OF THE INVENTION

One or more embodiments of the present disclosure include a navigation system for vascular intervention and a method of generating a virtual x-ray image, whereby a virtual x-ray image is generated from a 3-dimensional (3D) image to reduce an amount of x-rays exposed to a patient.

One or more embodiments of the present disclosure also include a navigation system for vascular intervention and a method of generating a virtual x-ray image, whereby an accurate surgery is performed by matching a local model of a 3D image to a virtual x-ray image or an actual x-ray image.

Additional aspects will be set forth in part in the description which follows and, in part, will be apparent from the description, or may be learned by practice of the presented embodiments.

According to one or more embodiments of the present disclosure, a method of generating a virtual x-ray image, the method includes: obtaining a 3-dimensional (3D) image of a patient; determining a projection direction of the 3D image in consideration of a position relationship between an x-ray source of an x-ray device and the patient; and generating a virtual x-ray image by projecting the 3D image on a 2D plane in the determined projection direction.

The determining of the projection direction of the 3D image may include determining the position relationship between the x-ray source and the patient by using first position information of a position finder with respect to an x-ray source sensor attached to the x-ray source, second position information of the position finder with respect to a patient sensor attached to the patient, and transformation relationship between reference coordinates of the x-ray source sensor and reference coordinates of the x-ray source.

The determining of the position relationship between the x-ray source and the patient may include calculating the transformation relationship between the reference coordinates of the x-ray source sensor and the reference coordinates of the x-ray source by using the first position information, third position information of the position finder with respect to a phantom sensor attached to a phantom, transformation relationship between reference coordinates of the phantom sensor and reference coordinates of the phantom, and transformation relationship between the reference coordinates of the phantom and the reference coordinates of the x-ray source.

The generating of the virtual x-ray image may include generating the virtual x-ray image by applying coordinates of each voxel of the 3D image to Equation 1: $T = I \cdot X^{-1} \cdot A^{-1} \cdot C \cdot R$, wherein I denotes an internal parameter indicating a position relationship between the x-ray source and a detector, X denotes the transformation relationship between the reference coordinates of the x-ray source sensor and the reference coordinates of the x-ray source, A denotes the first position information, C denotes the second position information, and R denotes a transformation relationship between reference coordinates of the patient sensor and reference coordinates of the 3D image.

The method may further include: determining a surgical instrument position from the 3D image based on position information of a surgical instrument based on a patient sensor attached to the patient; and displaying an identification mark on the determined surgical instrument position in the 3D image.

The determining of the surgical instrument position from the 3D image may include determining the surgical instrument position according to Equation 2: $N = R^{-1} \cdot C^{-1} \cdot F$, wherein N denotes coordinates of the surgical instrument position in the 3D image, R denotes reference coordinates of the patient sensor and reference coordinates of the 3D image, and E denotes fourth position of a position tracker with respect to the surgical instrument.

The method may further include calculating a transformation relationship between the reference coordinates of the patient sensor and the reference coordinates of the 3D image in consideration of coordinate information of a marker included in the 3D image, coordinate information of a position tracker with respect to a probe located on a marker of the patient, and the second information of the position finder with respect to the patient sensor.

The method may further include overlapping and displaying a local model of the 3D image on the generated virtual x-ray image.

According to one or more embodiments of the present disclosure, a navigation system is configured to: obtain a 3-dimensional (3D) image of a patient; determining a projection direction of the 3D image in consideration of a position relationship between an x-ray source of an x-ray device and the patient; generating a virtual x-ray image by projecting the 3D image on a 2D plane in the determined projection direction.

The navigation system may be further configured to display the generated virtual x-ray image on a screen or to match and display, on the screen, a local model of the 3D image to the generated virtual x-ray image.

According to one or more embodiments of the present disclosure, a navigation method performed by a navigation system, the navigation method includes: obtaining a 3-dimensional (3D) image of a patient; determining a projection direction of the 3D image in consideration of a position relationship between an x-ray source of an x-ray device and the patient; extracting a local model from the 3D image in consideration of the projection direction of the 3D image; and matching the extracted local model to an actual x-ray image obtained during a surgery performed on the patient.

BRIEF DESCRIPTION OF THE DRAWINGS

The above and other objects, features and other advantages of the present disclosure will be more clearly understood from the following detailed description taken in conjunction with the accompanying drawings, in which.

DESCRIPTION OF THE PREFERRED EMBODIMENTS

As the disclosure allows for various changes and numerous embodiments, particular embodiments will be illustrated in the drawings and described in detail in the written description. However, this is not intended to limit the present disclosure to particular modes of practice, and it will to be appreciated that all changes, equivalents, and substitutes that do not depart from the spirit and technical scope of the present disclosure are encompassed in the present disclosure.

In the description of the present disclosure, certain detailed explanations of related art are omitted when it is deemed that they may unnecessarily obscure the essence of the disclosure. While such terms as "first", "second", etc., may be used to describe various components, such components must not be limited to the above terms. The above terms are used only to distinguish one component from another.

In the specification, when a component is "connected" to or "accessing" another component, the component may be "directly connected" to or "directly accessing" the other component, but may also be connected to or accessing the other component via another component therebetween unless specifically stated otherwise.

Also, in the specification, regarding a component represented as a 'unit' or a 'module', two or more components may be combined as one component or one component may be divided into two or more components based on subdivided functions. Also, each of components described hereinafter may perform some or all functions performed by another component in addition to main functions, and some of the main functions of each of the components may be exclusively performed by another component.

Hereinafter, one or more embodiments the present disclosure will be described in detail with reference to accompanying drawings.

Figure 1:
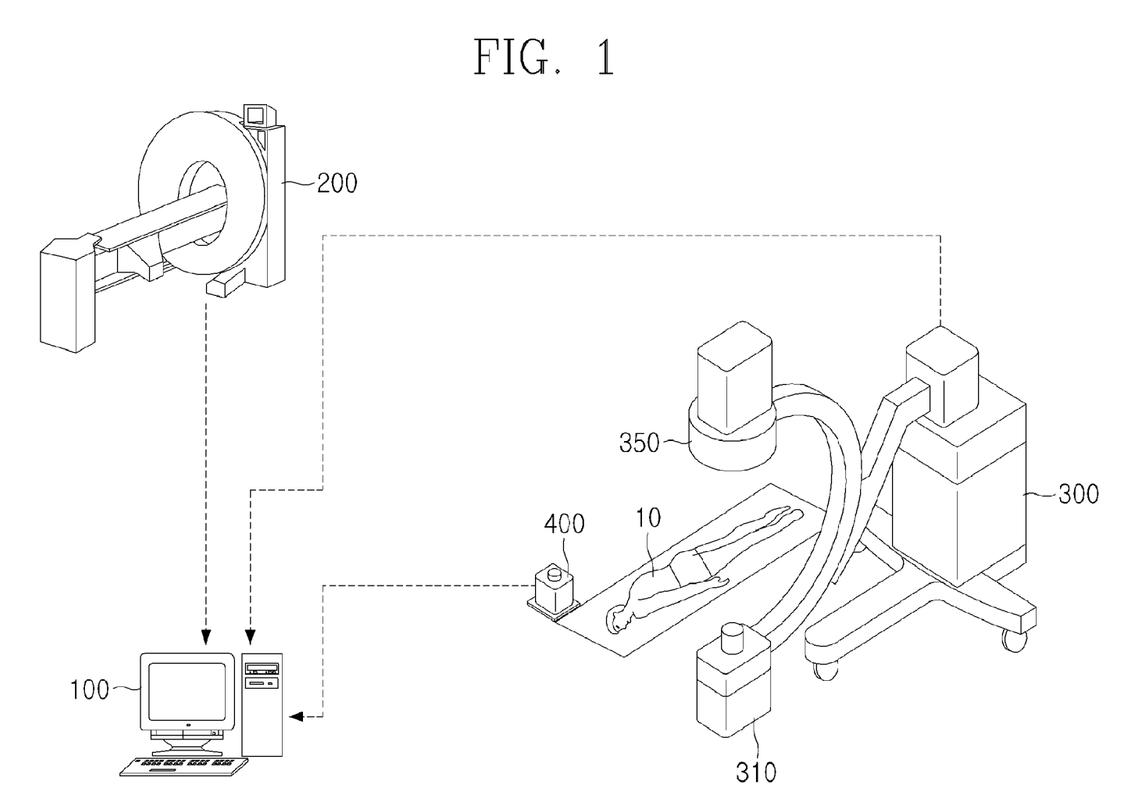
FIG. 1 illustrates an example of an environment to which a navigation system according to an embodiment of the present disclosure is applied.

FIG. 1 illustrates an example of an environment to which a navigation system 100 according to an embodiment of the present disclosure is applied.

The navigation system 100 according to an embodiment of the present disclosure may be realized by a general-purpose computer, and may include a communication function, an image processing function, and a displaying function. Also, the navigation system 100 may include a memory, a display, and a controller, wherein the memory and the controller may be realized by at least one processor and operate according to programs stored in the memory.

The navigation system 100 may receive a 3-dimensional (3D) image of a patient 10, which is captured by a 3D imaging apparatus 200, from the 3D imaging apparatus 200 or from another separate server. The 3D imaging apparatus may be a computed tomogrpahic angiography (CTA) apparatus, but is not limited thereto, and may be another apparatus as long as a 3D tomographic image of the patient 10 is obtained.

The patient 10 may receive vascular intervention in an imaging region of a C-arm type x-ray device 300, i.e., between an x-ray source 310 and a detector 350, and at this time, the navigation system 100 may derive a position relationship between the patient 10 and the x-ray source 310 of the x-ray device 300 from position information received from a position tracker 400, and generate and display a virtual x-ray image from the 3D image according to the derived position relationship.

An amount of radiation exposed to the patient 10 is massive during general vascular intervention because an x-ray image of the patient 10 is continuously captured, but according to an embodiment of the present disclosure, the amount of radiation exposed to the patient 10 may be largely reduced because a virtual x-ray image is generated from a 3D image pre-obtained before a surgery.

Also, according to an embodiment of the present disclosure, a local model (for example, a 3D vascular model that is a target of the surgery) of the 3D image may be matched to the virtual x-ray image, or the local model may be matched to an actual x-ray image captured by the x-ray device 300, such that an accurate 3D vascular structure of the patient 10 is notified to a medical team.

Meanwhile, as well known in the related fields, the C-arm type x-ray device 300 obtains a 2D image of the patient 10 when the x-ray source 310 irradiates x-rays onto a target object (i.e., the patient 10) and the detector 350 detects the x-rays accommodated by penetrating through the target object. In the specification, a 2D x-ray image generated from a 3D image is referred to as a 'virtual x-ray image', and a 2D x-ray image generated according to x-ray irradiation of the x-ray source 310 is referred to as an 'actual x-ray image'.

Hereinafter, processes of generating a virtual x-ray image will be described with reference to FIGS. 2 through 5.

Figure 2:
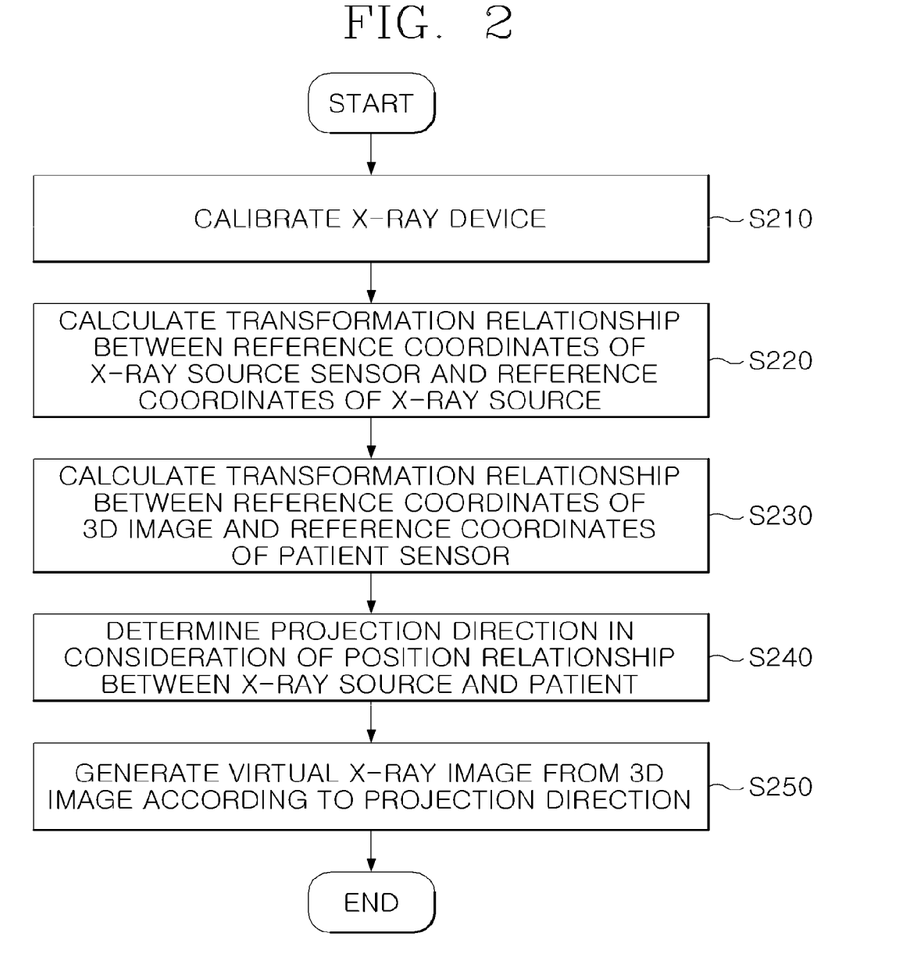
FIG. 2 is a flowchart of a method of generating a virtual x-ray image, according to an embodiment of the present disclosure.

FIG. 2 is a flowchart of a method of generating a virtual x-ray image, according to an embodiment of the present disclosure.

In operation S210, the navigation system 100 calibrates the x-ray device 300. The calibrating of the x-ray device 300 means that an internal parameter I and an external parameter E of the x-ray device 300 are obtained.

Figure 3:
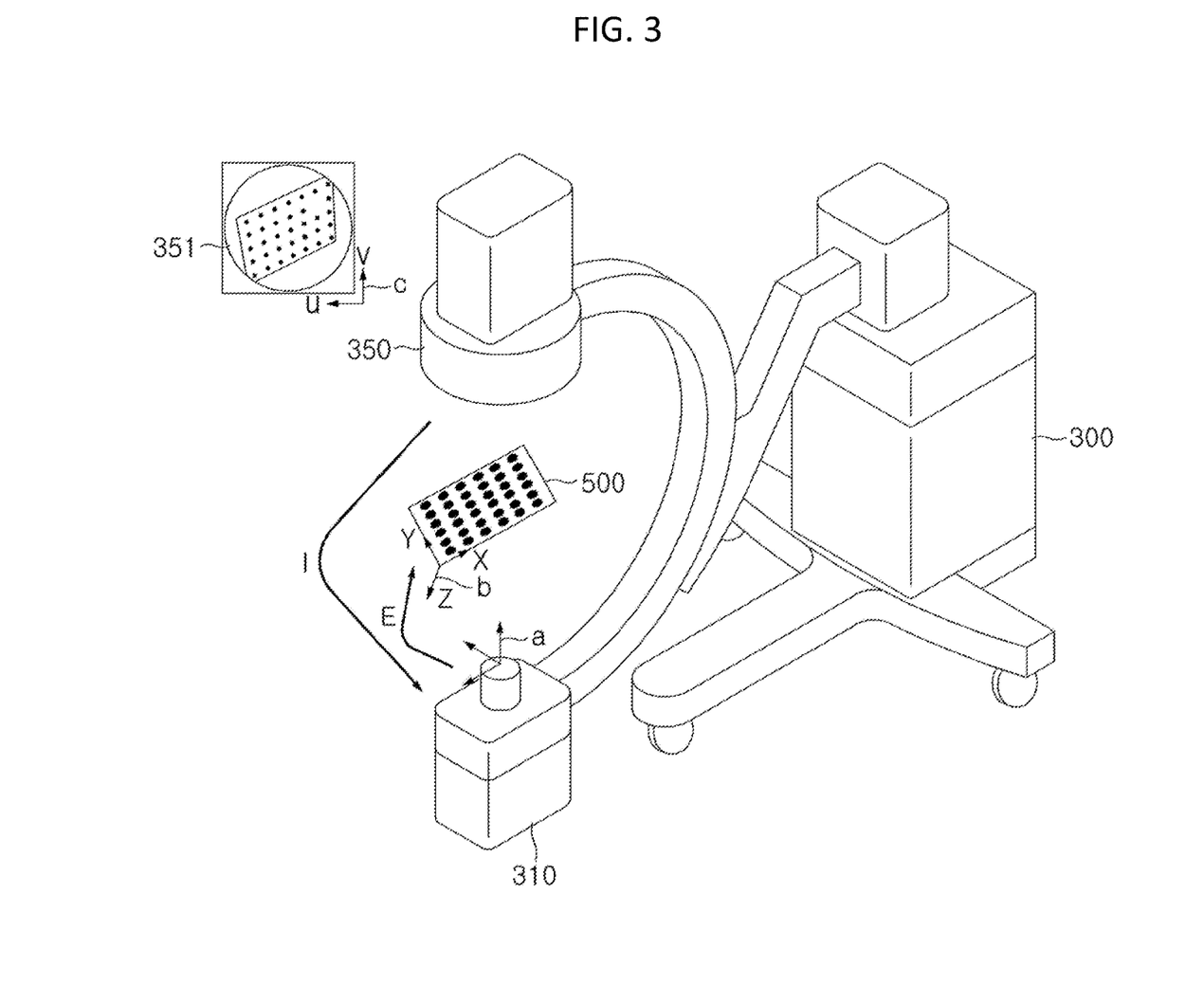
FIG. 3 is a diagram for describing a calibration method of an x-ray device.

Referring to FIG. 3, the internal parameter I corresponds to a transformation relationship between reference coordinates a of the x-ray source 310 and reference coordinates c of the detector 350. In FIG. 3, an arrow corresponding to the internal parameter I means that the internal parameter I includes relative movement information of the x-ray source 310 based on the detector 350. The internal parameter I may be represented by a matrix below.

[Internal Parameter]

$$\begin{bmatrix} \alpha_x & s & x_0 \\ 0 & \alpha_y & y_0 \\ 0 & 0 & 1 \end{bmatrix}$$

In the internal parameter I, $\alpha_x$ and $\alpha_y$ each denote a focal length corresponding to a vertical distance between the x-ray source 310 and the detector 350, wherein $\alpha_x$ denotes a value obtained by dividing a length between the x-ray source 310 and the detector 350 by a length of one of sides from among a height and a width of a pixel, and $\alpha_y$ denotes a value obtained by dividing the length between the x-ray source 310 and the detector 350 by a length of the other one of the sides from among the height and the width of the pixel. Also, $x_0$ and $y_0$ denote an image principal point indicating an offset distance between a center point of the detector 350 and a point where a center point of the x-ray source 310 is vertically projected onto the detector 350, and s denotes a skewness of the detector 350, i.e., a gradient between the width and the height of the pixel.

Also, referring to FIG. 3, the external parameter E corresponds to a transformation relationship between the reference coordinates a of the x-ray source 310 and reference coordinates b of a phantom 500 provided in an imaging region of the x-ray device 300. In FIG. 3, an arrow corresponding to the external parameter E means that the external parameter E includes relative movement and rotation information of the phantom 500 based on the x-ray source 310. The external parameter E may be represented by a matrix below.

[External Parameter]

$$\begin{bmatrix} r_{11} & r_{12} & r_{13} & t_1 \\ r_{21} & r_{22} & r_{23} & t_2 \\ r_{31} & r_{32} & r_{33} & t_3 \\ 0 & 0 & 0 & 1 \end{bmatrix}$$

In the matrix of the external parameter E, r denotes elements related to a rotation angle and t denotes elements related to a moving distance.

The internal parameter I may be pre-calculated and stored while manufacturing the x-ray device 300, and the external parameter E may be pre-calculated while positioning the phantom 500 in the imaging region of the x-ray device 300 (i.e., a region between the x-ray source 310 and the detector 350). According to an embodiment, the phantom 500 may be positioned in the imaging region and the internal parameter I and the external parameter E may be calculated based on an x-ray image 351 generated by capturing the phantom 500.

For example, when coordinates of a feature point of the phantom 500 based on the reference coordinates b of the phantom 500 are (x, y, z), and coordinates of the same feature point in an image of the phantom 500 based on the reference coordinates c of the detector 350 are (u, v), a relationship between the two coordinates may be represented as Equation 1.

$$w \begin{bmatrix} u \\ v \\ 1 \end{bmatrix} = P \cdot \begin{bmatrix} X \\ Y \\ Z \\ 1 \end{bmatrix} \qquad \text{[Equation 1]}$$

In Equation 1, w denotes a distance weight and P denotes a projection matrix of 3×4. When P is obtained through a single value decomposition (SVD) algorithm according to coordinate values of pre-known feature points, QR decomposition may b performed on the projection matrix P to obtain the internal parameter I and the external parameter E.

The internal parameter I may be used to generate a virtual x-ray image described later, and the external parameter E may be used to calculate a transformation relationship X between the reference coordinates h of an x-ray source sensor 410 and the reference coordinates a of the x-ray source 310.

Referring back to FIG. 2, in operation S220, the navigation system 100 calculates the transformation relationship X between the reference coordinates h of the x-ray source sensor 410 and the reference coordinates a of the x-ray source 310.

Figure 4:
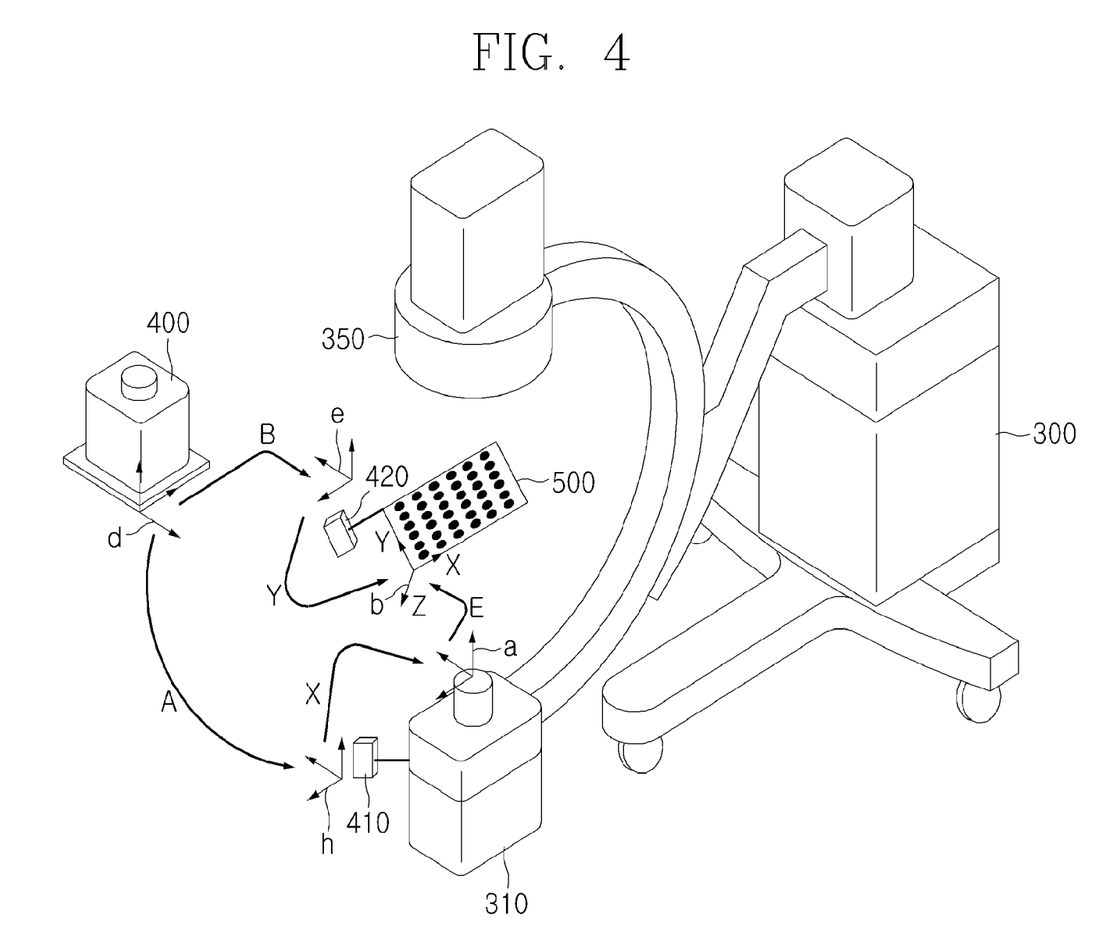
FIG. 4 is a diagram for describing a method of deriving a transformation relationship between reference coordinates of an x-ray source and reference coordinates of an x-ray source sensor.

Referring to FIG. 4, the x-ray source sensor 410 is attached to the x-ray source 310 and a phantom sensor 420 is attached to the phantom 500. The x-ray source sensor 410 and the phantom sensor 420 may be detected by the position tracker 400, and the position tracker 400 may detect the x-ray source sensor 410 and the phantom sensor 420 to generate position information.

For example, first position information A about the x-ray source sensor 410 attached to the x-ray source 310 and second position information B about the phantom sensor 420 attached to the phantom 500 are generated by the position tracker 400, and the first position information A and the second position information B are transmitted to the navigation system 100. The first position information A and the second position information B include relative movement information and relative rotation information of the x-ray source sensor 410 and the phantom sensor 420 based on reference coordinates d of the position tracker 400. A transformation relationship Y in FIG. 4 is a transformation relationship between reference coordinates e of the phantom sensor 420 and the reference coordinates b of the phantom 500, and is a value pre-determined when the phantom 500 is initially designed and installed. The transformation relationship Y includes relative movement information and relative rotation information of the phantom 500 based on the phantom sensor 420.

The navigation system 100 may derive the transformation relationship X between the reference coordinates h of the x-ray source sensor 410 and the reference coordinates a of the x-ray source 310 according to Equation 2, by using the first position information A, the second position information B, the transformation relationship Y, and the external parameter E. An arrow corresponding to the transformation relationship X in FIG. 4 means that the transformation relationship X includes relative movement and rotation information of the x-ray source 310 based on the x-ray source sensor 410.

$$A \cdot X = B \cdot Y \cdot E^{-1}$$

$$X = (A^{-1}) \cdot B \cdot Y \cdot (E^{-1}) \quad \text{[Equation 2]}$$

The relative movement and rotation information of the x-ray source 310, which changes via chain-multiplication of the first position information A of the position tracker 400 with respect to the x-ray source sensor 410 by the calculated transformation relationship X, may be determined in real-time based on the position tracker 400.

Referring back to FIG. 2, in operation 5230, the navigation system 100 calculates a transformation relationship R between reference coordinates g of a 3D image 210 and reference coordinates f of a patient sensor 430 attached to the patient 10.

Figure 5:
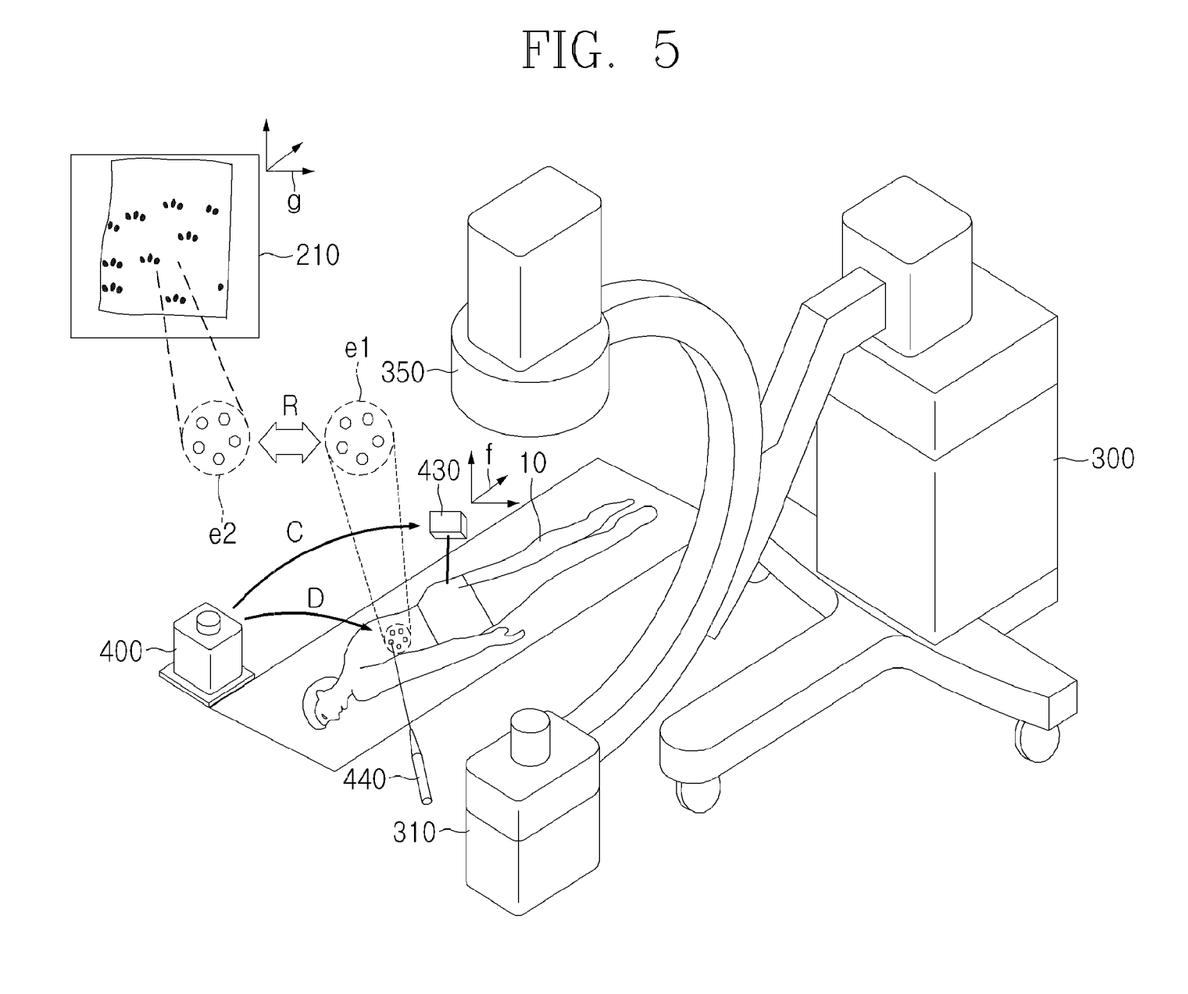
FIG. 5 is a diagram for describing a method of deriving a transformation relationship between reference coordinates of a patient sensor and reference coordinates of a 3-dimensional (3D) image.

In this regard, referring to FIG. 5, the patient sensor 430 that may be tracked by the position tracker 400 is attached to the patient 10. Also, a marker e1 that may be photographed by using the 3D imaging apparatus 200 may be attached to a body of the patient 10 before the 3D image 210 described above is generated, such that a marker e2 is included in the 3D image 210. In other words, before obtaining the 3D image 210 before the surgery, the marker e1 is attached to or inserted into the body of the patient 10. Coordinate information of the marker e2 included in the 3D image 210 may be identified based on the reference coordinates g of the 3D image 210.

Also, a probe 440 that may be tracked by the position tracker 440 may be brought near or brought into contact with the marker e1 attached to or inserted into the body of the patient 10 so as to obtain position information D of the probe 440 based on the position tracker 400.

Since the position tracker 400 may track the patient sensor 430, coordinate information of the probe 440 based on the reference coordinates f of the patient sensor 430 may be derived based on third position information C of the patient sensor 430 and the position information D of the probe 440.

The navigation system 100 may derive the transformation relationship R between the reference coordinates g of the 3D image 210 and the reference coordinates f of the patient sensor 430 through coordinate information of the marker e2 based on the reference coordinates g of the 3D image 210 and coordinate information of the marker e1 based on the reference coordinates f of the patient sensor 430, because positions of the probe 440 contacting the marker e2 in the 3D image 210 and the marker e1 are substantially the same. The transformation relationship R may include relative movement and rotation information of the 3D image 210 based on the patient sensor 430.

Referring back to FIG. 2, in operation 5240, the navigation system 100 determines a projection direction in consideration of a position relationship between the x-ray source 310 and the patient 10.

Figure 6:
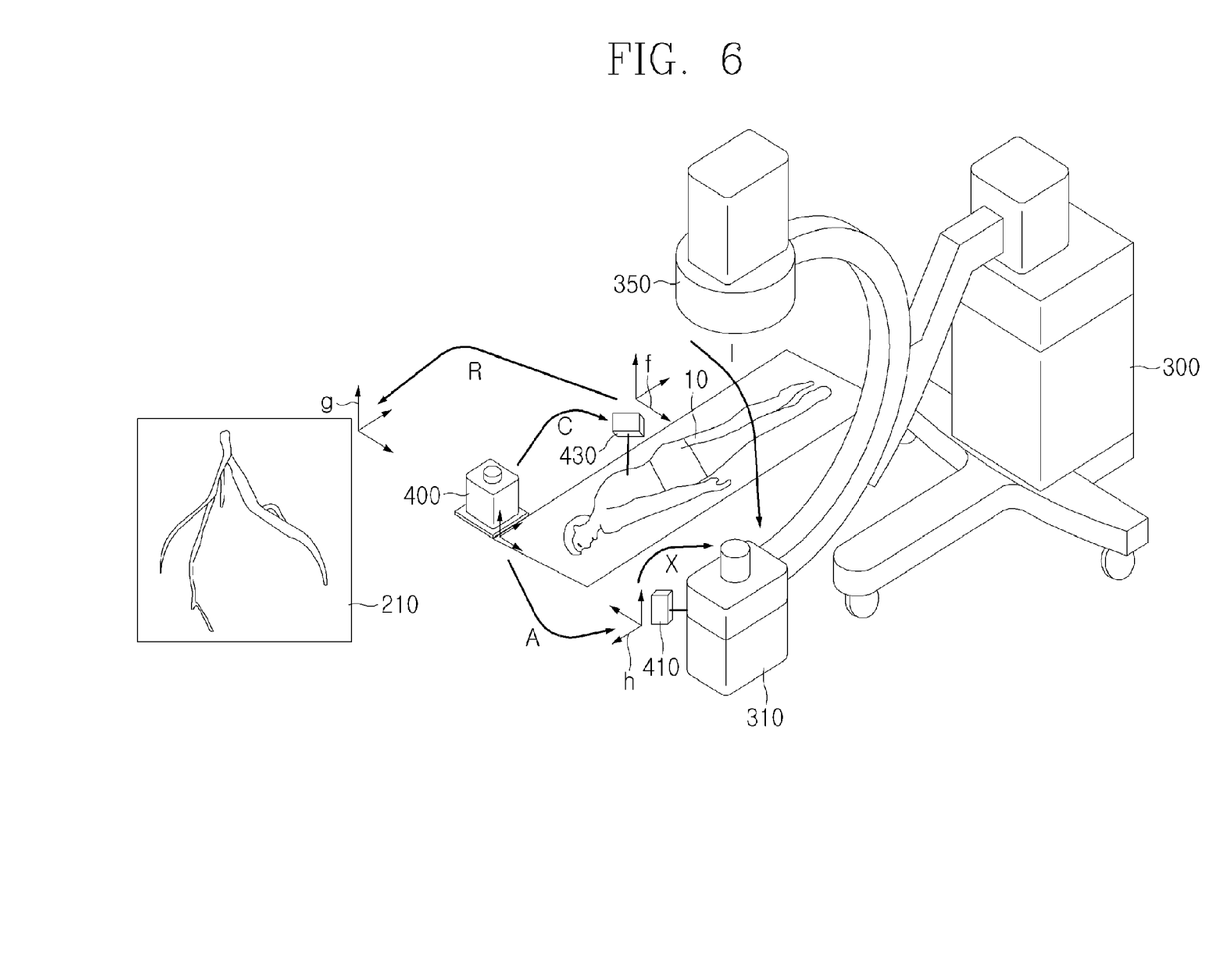
FIG. 6 is a diagram for describing a method of determining a projection direction of a 3D image according to a position relationship between a patient and an x-ray source.

In this regard, referring to FIG. 6, since the navigation system 100 is aware of the first position information A about the x-ray source sensor 410, the third position information C about the patient sensor 430, and the transformation relationship X between the x-ray source sensor 410 and the x-ray source 310, the navigation system 100 may derive a relative position relationship between the x-ray source 310 and the patient 10 (i.e., the patient sensor 430).

Also, since the navigation system 100 is aware of the transformation relationship R between the patient sensor 430 and the 3D image 210, the navigation system 100 may determine the projection direction of the 3D image 210 in consideration of the position relationship between the x-ray source 310 and the patient 10.

A projection direction M of the 3D image 210 may be represented as Equation 3.

$$M = X^{-1} \cdot A^{-1} \cdot C \cdot R \quad \text{[Equation 3]}$$

In operation 5250, the navigation system 100 generates a virtual x-ray image from the 3D image 210 according to the determined projection direction.

Since the projection direction of the 3D image 210 is determined in operation 5240, a transformation relationship T between the reference coordinates g of the 3D image 210 and the reference coordinates c of the detector 350 may be derived according to Equation 4 by using the internal parameter I indicating a relationship between the x-ray source 310 and the detector 350.

$$T = I \cdot M \quad \text{[Equation 4]}$$

The navigation system 100 may generate the virtual x-ray image from the 3D image 210 by using the transformation relationship T of Equation 4 since a location of a 2D plane (i.e., a virtual 2D plane corresponding to the detector 350) to which each voxel of the 3D image 210 is to be projected is determined by multiplying a coordinate value of each voxel in the 3D image 210 by the transformation relationship T.

Figure 7:
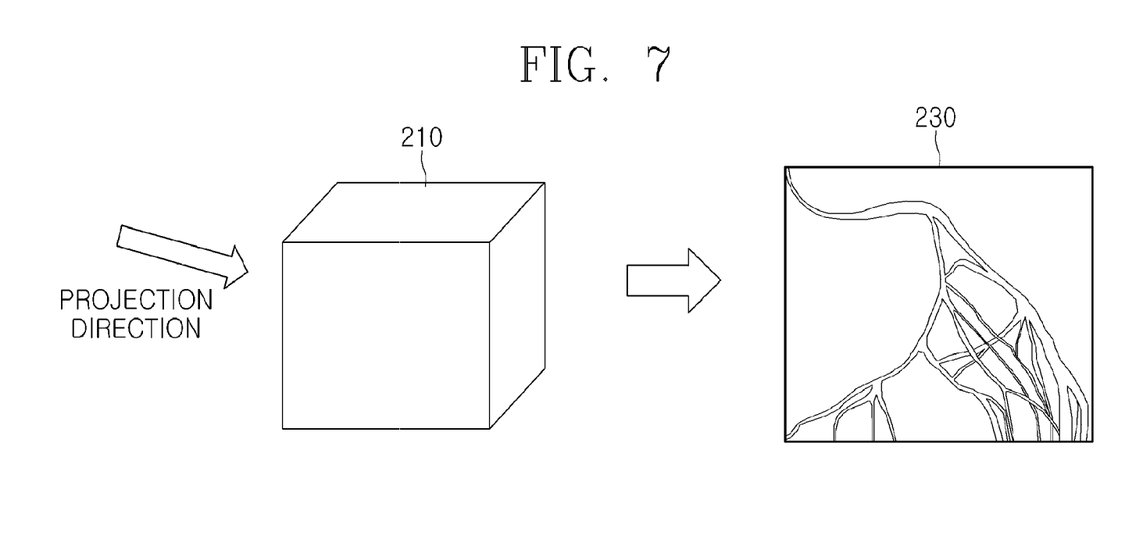
FIG. 7 is a diagram illustrating a projection direction of a 3D image and a virtual x-ray image generated from the 3D image.

As shown in FIG. 7, when the projection direction of the 3D image 210 is determined, a virtual x-ray image 230 that is the same as an actual x-ray image generated by irradiating x-rays in the projection direction may be generated.

Figure 8:
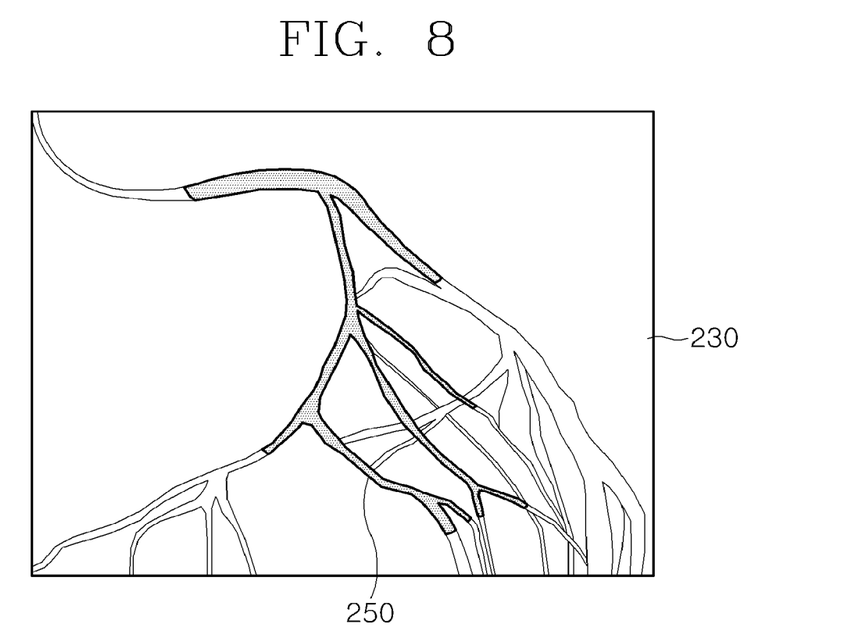
FIG. 8 illustrates an image in which a local model of a 3D image is overlapped on a virtual x-ray image.

According to an embodiment, a local model 250 of a 3D image may be matched to the virtual x-ray image 230 as shown in FIG. 8, or the local model 250 may be matched to an actual x-ray image of the patient 10 since a position relationship between the x-ray source 310 and the patient 10 is known and a projection direction of the 3D image 210 is determined accordingly. Thus, for example, even a region that is not identifiable from an x-ray image due to occlusion may be visualized.

Figure 9:
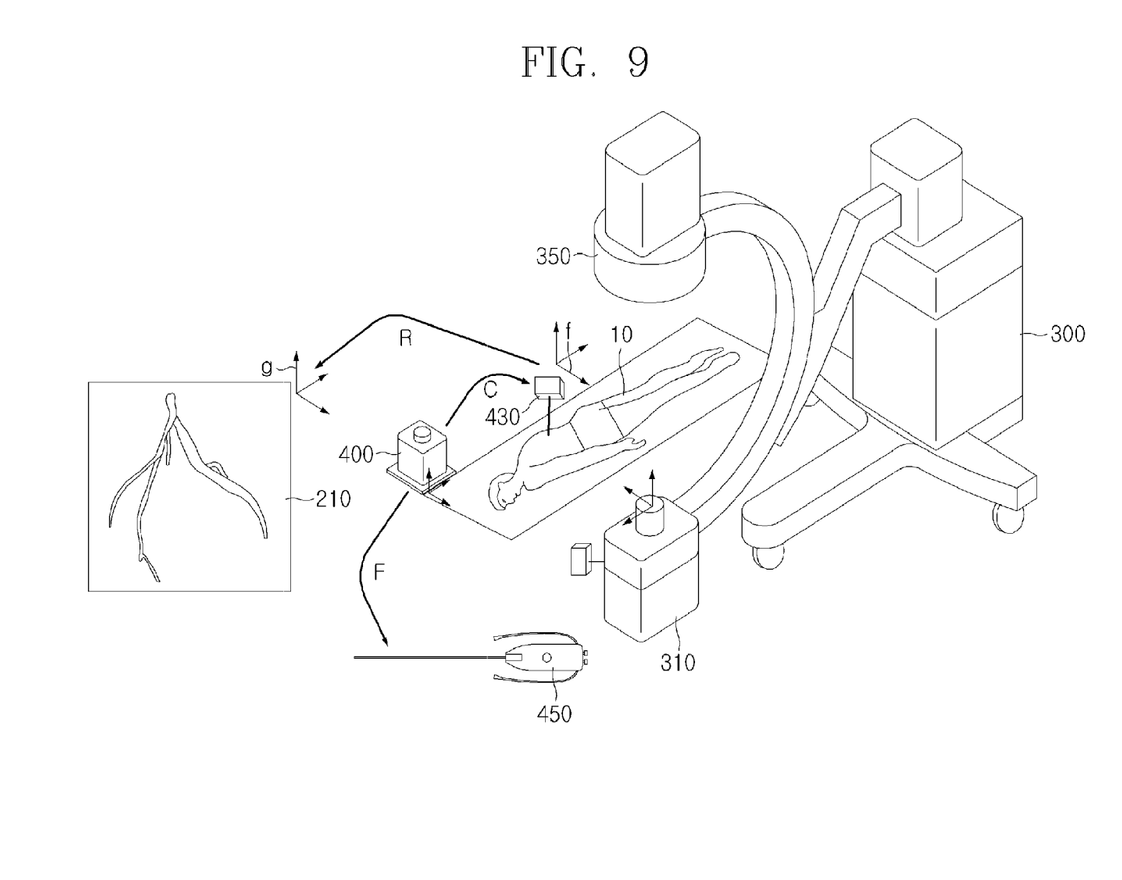
FIG. 9 is a diagram for describing a method of determining a position of a catheter in a 3D image.
Figure 10:
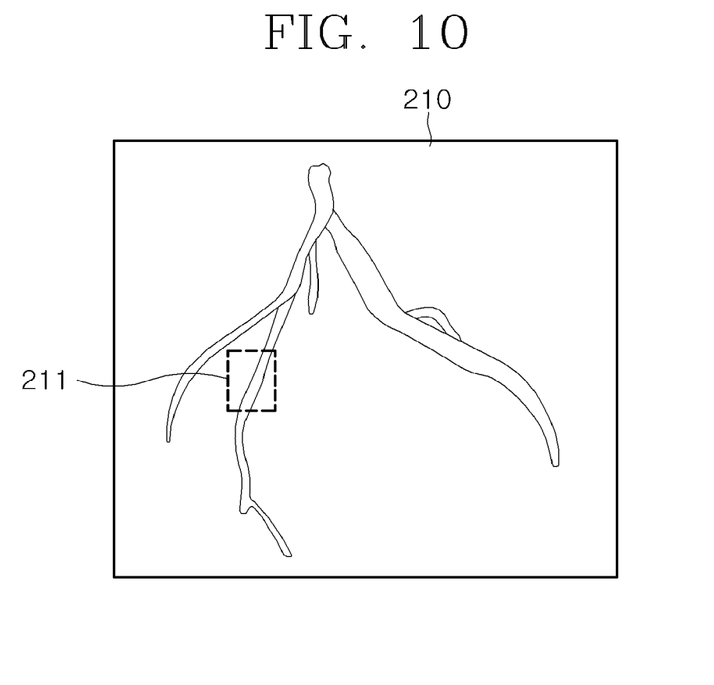
FIG. 10 illustrates a 3D image displaying an identification mark with respect to a position of a catheter.

FIGS. 9 and 10 are diagrams for describing a method of displaying position information of a catheter 450 on the 3D image 210.

When a catheter sensor (not shown) that is trackable by the position tracker 400 is attached to the catheter 450 and then the catheter 450 is inserted into blood vessels of the patient 10, position information F of the catheter 450 is generated by the position tracker 400.

Also, since the navigation system 100 is aware of the third position information C about the patient sensor 430, the navigation system 100 may derive coordinate information of the catheter 450 based on the reference coordinates f of the patient sensor 430. Also, since the navigation system 100 is aware of the transformation relationship R between the patient sensor 430 and the 3D image 210, the navigation system 100 may derive coordinate information of the catheter 450 on the 3D image 210, as is represented by Equation 5.

$$N = R^{-1} \cdot C^{-1} \cdot F \quad \text{[Equation 5]}$$

N denotes the coordinate information of the catheter 450 in the 3D image 210, and when position information of the catheter 450 is derived, the navigation system 100 may display an identification mark 211 on the catheter 340 determined in the 3D image 210 as shown in FIG. 10 so as to notify a medical team where the catheter 450 is positioned in the patent 10.

According to an embodiment, since the navigation system 100 is aware of a position relationship between the 3D image 210 and an x-ray image in consideration of a position relationship between the x-ray source 310 and the patient 10, the navigation system 100 may transform the coordinate information of the catheter 450 determined from the 3D image 210 to coordinate information in a 2D x-ray image, and display an identification mark in the 2D x-ray image. In other words, the medical team may determine a position of the catheter 450 from the 3D image 210 and/or the 2D x-ray image.

In FIGS. 9 and 10, the position of the catheter 450 is tracked, but the catheter 450 is only an example and a position of another type of surgical instrument in addition to the catheter 450 may be tracked by attaching a sensor.

A navigation system for vascular intervention and a method of generating a virtual x-ray image, according to one or more embodiments of the present disclosure, reduce an amount of x-rays exposed to a patient by generating a virtual x-ray image from a 3D image.

Also, a navigation system for vascular intervention and a method of generating a virtual x-ray image, according to one or more embodiments of the present disclosure, enable an accurate surgery by matching a local model of a 3D image to a virtual x-ray image or an actual x-ray image.

However, effects achievable by a navigation system for vascular intervention and a method of generating a virtual x-ray image, according to one or more embodiments of the present disclosure, are not limited thereto, and it would be obvious to one of ordinary skill in the art that the navigation system and the method may have other effects.

The embodiments of the present disclosure may be written as computer programs and may be implemented in general-use digital computers that execute the programs using a non-transitory computer-readable recording medium.

Examples of the non-transitory computer-readable recording medium include magnetic storage media (e.g., ROM, floppy disks, hard disks, etc.), optical recording media (e.g., CD-ROMs, or DVDs), etc.

Although preferred embodiments of the present disclosure have been described for illustrative purposes, those skilled in the art will appreciate that various modifications, additions and substitutions are possible, without departing from the scope and spirit of the invention as disclosed in the accompanying claims. Therefore, the embodiments of the present disclosure are disclosed only for illustrative purposes and should not be construed as limiting the present disclosure.

What is claimed is:

1. A method of generating a virtual x-ray image, the method comprising:
    obtaining a 3-dimensional (3D) image which comprising voxels of a patient;
    determining a projection direction of the 3D image based on a position relationship between an x-ray source of an x-ray device and the patient; and
    generating a virtual x-ray image of the patient by projecting the voxels of the 3D image of the patient on a 2D plane using a transformation of coordinates of each voxel of the voxels of the 3D image in the determined projection direction,
    wherein the virtual x-ray image is a 2D x-ray image generated from the 3D image, without irradiating x-ray,
    wherein the projection direction corresponds to the x-ray source's pointing direction to the patient, and
    wherein the generating of the virtual X-ray image comprises generating the virtual X-ray image by multiplying a coordinate of each voxel of the 3D image to relationship T in Equation below:

$$T = I \cdot X^{-1} \cdot A^{-1} \cdot C \cdot R$$

wherein I denotes a transformation relationship between a coordinate system of the X-ray source and a coordinate system of a detector, X denotes a transformation relationship between a coordinate system of an X-ray source sensor and the coordinate system of the X-ray source, A denotes position information of the X-ray source sensor in a coordinate system of a position tracker, C denotes position information of a patient sensor in the coordinate system of the position tracker, and R denotes a transformation relationship between a coordinate system of the patient sensor and a coordinate system of the 3D image.

2. The method of claim 1, wherein the determining of the projection direction of the 3D image comprises determining the position relationship between the x-ray source and the patient by using the position information of the x-ray source sensor attached to the x-ray source in the coordinate system of the position tracker, the position information of the patient sensor attached to the patient in the coordinate system of the position tracker, and the transformation relationship between the coordinate system of the x-ray source sensor and the coordinate system of the x-ray source,
    wherein positions of the x-ray source sensor and the patient sensor are trackable by the position tracker.

3. The method of claim 2, wherein the determining of the position relationship comprises calculating the transformation relationship between the coordinate system of the X-ray source sensor and the coordinate system of the X-ray source by using the position information of the X-ray source sensor in the coordinate system of the position tracker, position information of a phantom sensor attached to a phantom in the coordinate system of the position tracker, transformation relationship between a coordinate system of the phantom sensor and a coordinate system of the phantom, and transformation relationship between the coordinate system of the phantom and the coordinate system of the x-ray source, wherein the phantom sensor is trackable by the position tracker.

4. The method of claim 1, further comprising:
    determining a surgical instrument position of a surgical instrument in the 3D image based on position information of the surgical instrument based with respect to the patient sensor attached to the patient; and displaying an identification mark on the surgical instrument position determined in the 3D image.

5. The method of claim 4, wherein the determining of the surgical instrument position from the 3D image comprises determining the surgical instrument position according to Equation below:

$$N = R^{-1} \cdot C^{-1} \cdot F,$$

wherein N denotes position information of the surgical instrument position in a coordinate system of the 3D image, R denotes the transformation relationship between the coordinate system of the patient sensor and the coordinate system of the 3D image, and F denotes position information of the surgical instrument in the coordinate system of the position tracker, wherein the surgical instrument and the patient sensor are trackable by the position tracker.

6. The method of claim 3, further comprising calculating the transformation relationship between the coordinate system of the patient sensor and the coordinate system of the 3D image, based on position information of a probe placed adjacent to a marker, which is attached to the patient to mark a predetermined position of a body of the patient, in the coordinate system of the position tracker, position information of the marker captured in the 3D image in the coordination system of the 3D image, and the position information of the patient sensor in the coordinate system of the position tracker.

7. The method of claim 1, further comprising overlapping and displaying a local model of the 3D image on the generated virtual x-ray image.

8. A navigation system configured to:

obtain a 3-dimensional (3D) image, which comprising voxels, of a patient;

determine a projection direction of the 3D image in consideration of a position relationship between an x-ray source of an x-ray device and the patient;

generate a virtual x-ray image of the patient by projecting the voxels of the 3D image of the patient on a 2D plane using a transformation of coordinates of each voxel of the voxels of the 3D image of the patient in the determined projection direction, wherein the virtual X-ray image is a 2D X-ray image generated from the 3D image, without irradiating X-ray, and wherein the generating of the virtual X-ray image comprises generating the virtual X-ray image by multiplying a coordinate of each voxel of the 3D image to relationship T in Equation below:

$$T = I \cdot X^{-1} \cdot A^{-1} \cdot C \cdot R$$

wherein I denotes a transformation relationship between a coordinate system of the X-ray source and a coordinate system of a detector, X denotes a transformation relationship between a coordinate system of an X-ray source sensor and the coordinate system of the X-ray source, A denotes a position information of the X-ray source sensor in a coordinate system of a position tracker, C denotes a position information of a patient sensor in the coordinate system of the position tracker, and R denotes a transformation relationship between a coordinate system of the patient sensor and a coordinate system of the 3D image.

9. The navigation system of claim 8, further configured to display the generated virtual X-ray image and a local model of the 3D image matching the generated virtual X-ray image in an overlapping manner.

10. A navigation method performed by a navigation system, the navigation method comprising:

obtaining a 3-dimensional (3D) image of a patient;

determining a projection direction of the 3D image in consideration of a position relationship between an x-ray source of an x-ray device and the patient;

extracting a local model from the 3D image in consideration of the projection direction of the 3D image; and matching the extracted local model and a position of a surgical instrument to a virtual x-ray image, which is a 2D x-ray image, which is of the patient, generated without irradiating x-ray from the 3D image of the patient based on the projection direction during a surgery performed on the patient, and wherein the generating of the virtual X-ray image comprises generating the virtual X-ray image by multiplying a coordinate of each voxel of the 3D image to relationship T in Equation below:

$$T = I \cdot X^{-1} \cdot A^{-1} \cdot C \cdot R$$

wherein I denotes a transformation relationship between a coordinate system of the X-ray source and a coordinate system of a detector, X denotes a transformation relationship between a coordinate system of an X-ray source sensor and the coordinate system of the X-ray source, A denotes a position information of the X-ray source sensor in a coordinate system of a position tracker, C denotes a position information of a patient sensor in the coordinate system of the position tracker, and R denotes a transformation relationship between a coordinate system of the patient sensor and a coordinate system of the 3D image.

11. A non-transitory computer-readable recording medium having recorded thereon a program which, when executed by a computer, performs the method of claim 1.

* * * * *